US00PP20960P2

(12) United States Plant Patent
Austin

(10) Patent No.: US PP20,960 P2
(45) Date of Patent: Apr. 27, 2010

(54) ***ROSA HYBRIDA* SHRUB NAMED 'AUSVIBRANT'**

(50) Latin Name: *Rosa hybrida*
Varietal Denomination: AUSvibrant

(75) Inventor: David C. H. Austin, Wolverhampton (GB)

(73) Assignee: David Austin Roses Ltd, Albrighton, Wolverhampton (GB)

( * ) Notice: Subject to any disclaimer, the term of this patent is extended or adjusted under 35 U.S.C. 154(b) by 0 days.

(21) Appl. No.: 12/381,337

(22) Filed: Mar. 11, 2009

(30) Foreign Application Priority Data

Nov. 18, 2008 (GB) ..... AFP 5/2108

(51) Int. Cl.
*A01H 5/00* (2006.01)

(52) U.S. Cl. ..... Plt./102

(58) Field of Classification Search ..... Plt./102
See application file for complete search history.

*Primary Examiner*—Annette H Para
(74) *Attorney, Agent, or Firm*—Kauth, Pomeroy, Peck & Bailey LLP

(57) ABSTRACT

A variety of rose plant of the shrub class, named 'AUSvibrant' is disclosed. The 'AUSvibrant' rose is a plant suitable for repeat flowering production having large deeply cupped blooms having a color blend of deep magenta, pink and red, with an unusual fragrance which develops from Tea into Old Rose.

1 Drawing Sheet

CROSS-REFERENCE TO RELATED APPLICATIONS

The current application claims priority to a United Kingdom Breeder's Right Certificate Application No. AFP 5/2108 filed Nov. 18, 2008, the disclosure of which is incorporated herein by reference.

Classification: The present invention relates to a new *Rosa hybrida* shrub.

Variety denomination: The new plant has the varietal denomination 'AUSvibrant'.

ORIGIN OF INVENTION

This invention relates to a new and distinct variety of shrub rose plant named 'AUSvibrant', which was originated by crossing two unnamed, unpatented varieties of *Rosa hybrida.*

BACKGROUND OF THE INVENTION

The primary objective of this breeding was to produce a flowering variety having large deeply cupped blooms with many petals arranged in an informal way, and having a deep magenta color.

SUMMARY OF THE INVENTION

Among the features which distinguish the new variety from other presently available and commercial rose cultivars known to the inventor is the following combination of characteristics: large deeply cupped blooms having a color blend of deep magenta, pink and red, with an unusual fragrance which develops from Tea into Old Rose.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSvibrant' may be asexually propagated by budding and grafting. The budding and grafting successfully occurred on the plant/rootstock Rosa cv. 'Dr. Huey' in the United States and on the plant/rootstock *Rosa dumetorum* cv. 'Laxa' in the United Kingdom.

COMPARISON WITH PARENTS

The new rose may be distinguished from its seed parent, by the following combination of characteristics: whereas the seed parent has medium-sized pink blooms and upright short growth, 'AUSvibrant' produces a much larger bloom of deep magenta. The new variety is classified as a *hybrida* rose.

The new variety may be distinguished from its pollen parent, by the following combination of characteristics: whereas the pollen parent bears smaller crimson blooms with few petals, 'AUSvibrant' bears large size flowers of deep magenta having many petals.

COMPARISON WITH THE CLOSEST COMMERCIALLY AVAILABLE CULTIVAR

The closest commercially available cultivar to the new variety is the 'AUSintense' (U.S. Pat. No. 16,763). The new rose may be distinguished from the 'AUSintense' variety by the following combination of characteristics: the 'AUSintense' has a quartered shallow cup and smaller blooms compared to 'AUSvibrant', which has broader blooms having a deep cup and bearing more rounded petals. In addition, the 'AUSintense' variety has a strong Old Rose fragrance, while the 'AUSvibrant' starts out as Tea and develops into Old Rose.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

The following description is of 2-year-old rose plants of the new variety grown outdoors in Albrighton, Britain in the month of August. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 2.3 cm long and 2 cm in diameter when the petals start to unfurl. Form: The bud form is short and broad based. Color: When sepals first divide, the bud color is Red-Purple Group 59B. When half blown, the upper sides of the petals are Red-Purple Group 64B, and the lower sides of the petals are Red-Purple Group 64B with Red-Purple Group N74D. Calyx: Shape: Funnel. Length: 1.8 cm. Diameter: 2.5 cm. Sepals: Arrangement: Regular. Color: Upper Surface: Yellow-Green Group N144A. Lower Surface: Yellow-Green Group 147D. Length: 2.5 cm. Width: 1 cm. Shape: Acuminate with medium extensions. Margin: Smooth. Surface texture: Upper Surface: Smooth. Lower Surface: Downy. Number: There are three lightly appendaged sepals. There are 2 unappendaged sepals with smooth edges. Receptacles: Color: Yellow-Green Group N144A. Shape: Funnel. Size: Broad, about 0.8 cm tall×1.2 cm wide. Surface: Smooth. Peduncle: Length: Medium, averaging about 6 cm. Surface: Smooth. Color: Green Group 137B tinged with Greyed-Red Group 178B. Strength: Strong.

*Blooms.*—Size: Very large, average open diameter is about 10.5 cm. Borne: Several together in clusters of 4–6 blooms having an irregular shape. Stems: Strength: Normal, average length is about 20 cm. Diameter: 5 mm. Form: When first open, bloom is cupped. Permanence of bloom: retains its form to the end.

*Petalage.*—Number of petals under normal conditions: about 90. Color: The upper sides of the petals are Red-Purple Group 64B. The reverse sides of the petals are Purple Group 75A. The base of the petals has a spot of Yellow Group 1D. Discoloration: The general tonality at the end of the first to third days is Red-Purple Group 64B. With further aging the color changes to: Red-Purple Group 70B. Fragrance: Strong. Character of fragrance: Tea developing into Old Rose.

*Petals.*—Texture: Smooth, velvety. Size: Width: 4 cm. Length: 5 cm. Surface: Smooth. Shape: Round. Margin: Most are entire, though some outer petals are notched. Apex Shape: Rounded. Base Shape: Ovate. Form: Incurved. Arrangement: Informal. Petaloids: Number: 10. Color: Red-Purple Group 64A; Length: 14 mm. Width: 5 mm. Shape: Irregular. Margin: Irregular. Persistence: Petals drop off cleanly before drying. Lastingness: On the plant: fair, about 7 days. As a cut flower: not tested.

*Reproductive parts.*—Stamens: Number: 45. Length: 8 mm. Anthers: Length: 4 mm. Color: Yellow Group 2C. Arrangement: Regular around styles. Filaments: Color: White Group 155B. Length: 4 mm. Pollen: Color: Yellow-Orange Group 17A. Pistils: Number: 53. Length: 9 mm. Styles: Color: Yellow Group 2D. Length: 7 mm. Stigmas: Color: Green-White Group 2D. Length: 9 mm. Hips: None Observed.

Plant characteristics:

*Plant form.*—Shrub.

*Plant growth.*—Vigorous.

*Age to maturity.*—Two years.

*Mature plant.*—Height: 1.2 m. Width: 0.9 m.

*Rootstock.*—*Rosa* 'Dr. Huey' for U.S. and *Rosa dumetorum* cv. 'Laxa' for observed plants in the U.K.

*Foliage.*—Number: Leaflets on normal mid-stem leaves: 5 (including terminal leaflet). Size: Medium, about 13.5 cm long×10.5 cm wide. Quantity: Abundant. Number of leaves per flowering stem: 10. Color: New foliage: Upper side: Green Group 143B, overlaid with Greyed-Purple Group 184B. Lower side: Green Group 148B overlaid with Greyed-Purple Group 184B. Old foliage: Upper side: Green Group 137A. Lower side: Green Group 138B.

*Leaflets.*—Size: About 13 cm long×10.5 cm wide. Shape: Broadly oval. Base Shape: Rounded. Apex Shape: Acuminate. Texture: Leathery. Edge: Serrated. Serrations: Single large. Petiole: Color: Green Group 137A. Length: 3.1 cm. Width: 1.3 mm. Surface Texture: With prickles. Petiole Rachis: Color: Green Group 137A. Underside: With prickles. Stipules: Length: 2 cm, glandular. Color: Green Group 137B. Auricle: Shape: Sword shaped. Length: 8 mm. Width: 1 mm. Color: Green Group 137B. Vein Color: As leaf color Green Group 137B. Venation Pattern: Net-veined.

*Wood.*—New Wood: Color: Greyed-Red Group 178B. Bark: Smooth. Old Wood: Color: Green Group 137B with Greyed-Red Group 178B. Bark: smooth.

*Branching habit.*—Number: 8 per main stem. Lateral Branch Dimensions: Length: 25 cm. Diameter: 4 mm.

*Stems.*—Mature Stem: Length: 45 cm. Diameter: 6 mm. Internode Distance: 40 mm. The above measurements are all variable, depending on growing conditions in a season. Stem Pubescence Present: No.

*Prickles.*—Quantity: On main canes from base: Few. Number per stem length: 6 per 10 cm. On laterals from main canes: Few. Number per stem length: 6 per 10 cm. Form: Deep concave. Length: 7 mm. Color when young: Greyed-Red Group 183A. Color when mature: Greyed-Red Group 178A.

*Small prickles.*—Quantity: Main stalk: Few. Number per stem length: 5 in top third section of stem. Laterals: None. Color: When young: Greyed-Red Group 183A. When mature: Greyed-Red Group 178A.

*Disease resistance.*—Mildew: Resistant. Blackspot: Resistant. Rust: Resistant.

*Pest resistance.*—Not tested.

*Winter hardiness.*—Not tested.

*Growing conditions.*—Normal.

What is claimed is:

1. A new and distinct variety of rose plant of the shrub class suitable for repeat flower production, substantially as herein shown and described.

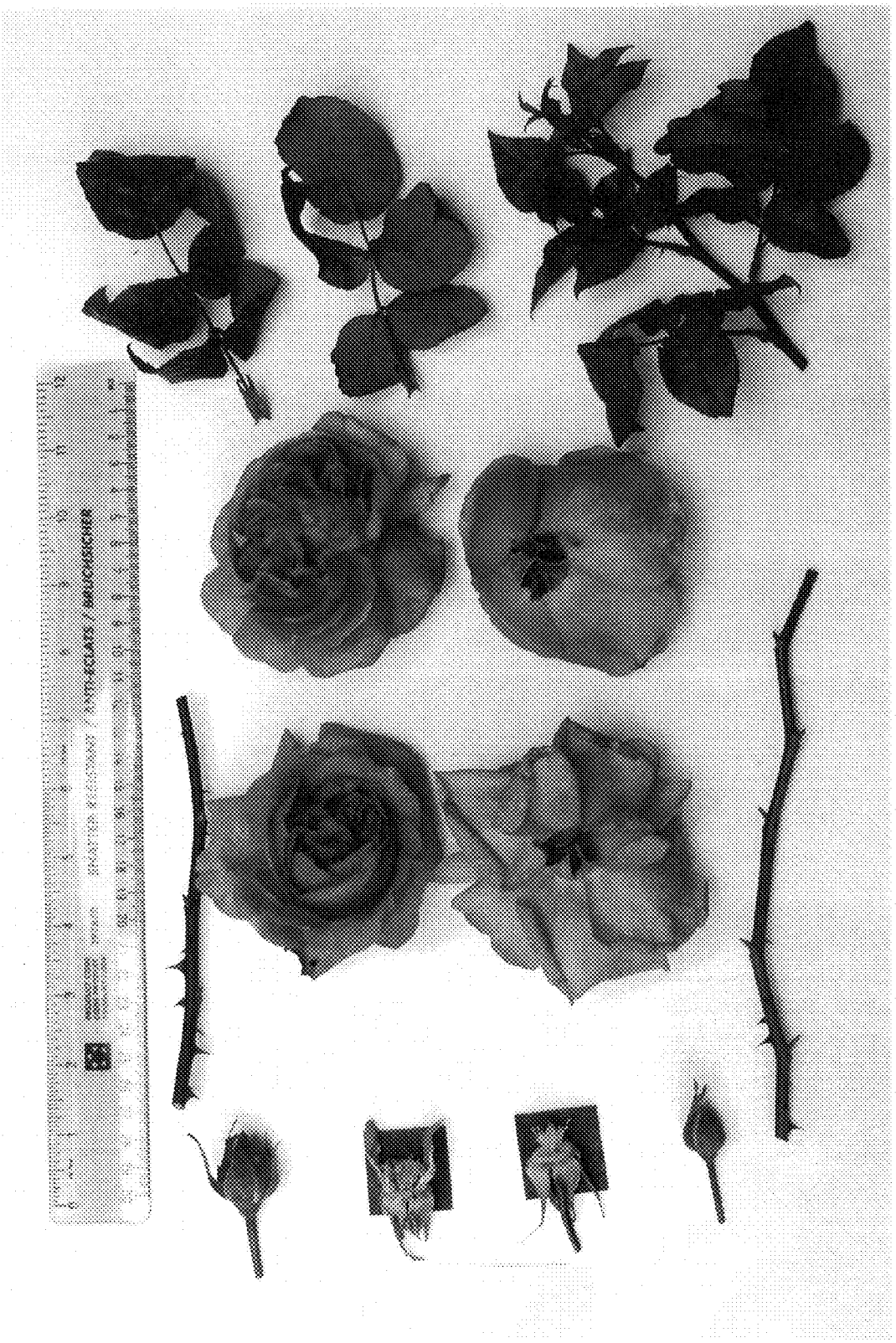

* * * * *